(12) United States Patent
Schneider et al.

(10) Patent No.: US 6,645,514 B1
(45) Date of Patent: Nov. 11, 2003

(54) INCREASING SKIN CELL RENEWAL WITH WATER-SOLUBLE VITAMIN E

(75) Inventors: Louise M. Schneider, Rockford, MI (US); Melissa L. Hundey, Grand Rapids, MI (US); John V. Scimeca, Kentwood, MI (US)

(73) Assignee: Access Business Group International, LLC, Ada, MI (US)

( * ) Notice: Subject to any disclaimer, the term of this patent is extended or adjusted under 35 U.S.C. 154(b) by 0 days.

(21) Appl. No.: 10/325,326

(22) Filed: Dec. 19, 2002

(51) Int. Cl.$^7$ ................................................. A61K 7/48
(52) U.S. Cl. ..................... 424/401; 514/458; 514/844; 514/944
(58) Field of Search .................. 424/401; 514/458, 514/844, 944

(56) References Cited

U.S. PATENT DOCUMENTS

| | | | |
|---|---|---|---|
| 5,306,713 A | 4/1994 | Suetsugu et al. | 514/100 |
| 5,387,579 A | 2/1995 | Meybeck et al. | 514/100 |
| 5,603,949 A | 2/1997 | Meybeck et al. | 424/450 |
| 5,643,597 A | 7/1997 | Meybeck et al. | 424/450 |
| 5,656,618 A | 8/1997 | Meybeck et al. | 514/100 |
| 5,952,001 A | 9/1999 | Meybeck et al. | 424/450 |
| 6,008,246 A | 12/1999 | Ito et al. | 514/458 |
| 6,022,867 A | 2/2000 | Ito et al. | 514/100 |
| 6,136,851 A | 10/2000 | Bonte et al. | 514/458 |
| 6,184,247 B1 | 2/2001 | Schneider | 514/474 |
| 6,248,779 B1 | 6/2001 | Shimizu et al. | 514/458 |

FOREIGN PATENT DOCUMENTS

| | | |
|---|---|---|
| EP | 0 236 120 | 8/1992 |
| EP | 0 513 104 | 1/1996 |
| EP | 0 780 116 | 6/1997 |
| EP | 0 679 399 | 8/1997 |
| EP | 0 652 010 | 1/1998 |
| EP | 0 597 025 | 9/1998 |
| EP | 0911016 A1 | 4/1999 |
| JP | 3109308 A2 | 5/1991 |
| JP | 3275610 A2 | 12/1991 |
| JP | 5331020 A2 | 12/1993 |
| JP | 6024931 A2 | 2/1994 |
| JP | 9118613 A2 | 5/1997 |
| JP | 10007524 A2 | 1/1998 |
| JP | 10007541 A2 | 1/1998 |
| JP | 11189523 A2 | 7/1999 |
| JP | 11228378 A2 | 8/1999 |
| JP | 2000256173 A2 | 9/2000 |
| JP | 2000290131 | 10/2000 |
| JP | 2000290132 | 10/2000 |
| JP | 2000290133 | 10/2000 |
| JP | 2000290134 | 10/2000 |
| WO | WO 93/15731 | 8/1993 |

OTHER PUBLICATIONS

Loden, Marie, "*Dry Skin and Moisturizers—Chemistry and Function*", Dermatology: Clinical & Basic Science Series, CRC Press (2000) pp. 1–168.
*Cosmetic Dermatology*, 347 pages.
Smith, Walter P., "*Hydroxy Acids and Skin Aging*", Soap/Cosmetics/Chemical Specialties, Sep. 1993, pp. 54–76.
Yu, Ruey, Jr. et al., "*Bioavailability of Alpha–Hydroxy Acids in Topical Formulations*", Cosmetic Dermatology, vol. 9, No. 6, Jun. 1996, (5p.).
*Technical Information on Vitamin E Phosphate (VEP)*, Central Research Laboratory & Specialty Chemical Division, Showa Denko K.K., Dec. 2000, (23 p.).

*Primary Examiner*—Jyothsna Venkat
(74) *Attorney, Agent, or Firm*—Brinks Hofer Gilson & Lione

(57) ABSTRACT

The present invention relates to a method of enhancing the rate of skin exfoliation by incorporating a water-soluble Vitamin E derivative into a cosmetic composition that contains water and is suitable for application to mammalian skin. The composition has a pH from about 4.5 to 9 and can increase the rate of natural skin exfoliation by at least 10%.

16 Claims, No Drawings

INCREASING SKIN CELL RENEWAL WITH WATER-SOLUBLE VITAMIN E

BACKGROUND OF THE INVENTION

Human skin is continually assaulted by environmental conditions such as the sun, wind, and pollution. These environmental assaults age the visible layer of skin and reduce. the ability of the skin to serve as an effective barrier layer against the environment. This weathering causes undesirable conditions that include wrinkles, age spots, roughness, scaling, flaking, uneven appearance,.and uneven coloration. In addition, the effects of natural aging also cause the skin to wrinkle.

These negative effects can be prevented, or at least ameliorated, by applying skin care cosmetics that contain skin benefit agents that increase exfoliation according to the present invention.

Human skin may be classified into two major parts: the outer layer or epidermis and an underlying layer or dermis. The dermis contains, among other things, blood vessels, nerves, collagen, elastin, and fibroblast cells, which are responsible for the biosynthesis of collagen and elastin.

The epidermis may be considered to consist of two major zones, an inner or malpighian layer, and an outer or horny layer. The inner malpighian layer, a living tissue, may be further divided into basal, spinous, and granular layers. The outer horny layer, a dead tissue, is also referred to as stratum corneum.

In the natural skin renewal process, basal cells move outward from the basal layer and pass through the spinous and granular layers to become dead cells called corneocytes, in the stratum corneum. This process of forming corneocytes is called keratinization. The stratum corneum consists of approximately 14 layers of dead cells and is the skin tissue that one feels when touching the surface of the skin.

In normal skin, it takes about 14 days for the basal cells to move from the basal layer to the end of the granular layer and to become corneocytes, and another 14 days for the corneocytes to reach the outermost layer of the stratum corneum, where they are naturally shed or exfoliated. Thus, it takes about 28 days for cells of the basal layer to move outward to the surface in the course of skin renewal.

Based on this understanding of skin behavior, two common methods are used to improve the appearance of the skin through the application of topical compositions. In the first, a composition is applied that protects the living portion of the skin from damage. In the second, a composition is applied that increases the natural exfoliation rate (cell renewal rate) of the skin, thus increasing the rate at which the outer layers of dead cells (the stratum corneum) are replaced.

One conventional method of protecting the living skin cells from oxidative damage is by applying a composition containing α-Tocopherol (naturally occurring Vitamin E) to the surface of the skin. Naturally occurring Vitamin E is oil-soluble and can improve the appearance of the skin through continued use by penetrating the outer layers of the skin to protect the living skin cells from oxidative attack, such as from radicals and peroxides. Additional oil-soluble Vitamin E derivatives, including ester derivatized Vitamin E, Tocopheryl Acetate, Tocopheryl Linoleate, Tocopheryl Linoleate/Oleate, Tocopheryl Nicotinate, and Tocopherol (vitamin E alcohol), can also serve to protect living skin cells from oxidative attack. Naturally occurring Vitamin E and its oil-soluble derivatives are believed to improve the appearance of skin by reducing oxidative damage to living cells. These oil-soluble preparations are not known ;to increase exfoliation (skin cell-renewal) rate.

Unlike oil-soluble vitamin E derivatives, water soluble vitamin E derivatives are known to prevent damage to organs when administered internally. U.S. Pat. No. 6,022,867, the entire contents of which is incorporated herein by reference, except that in the event of any inconsistent disclosure or definition from the present application, the disclosure or definition herein shall prevail, describes a water-soluble Vitamin E derivative, DL-α-Tocopheryl Phosphate (VEP). The derivative is prepared by reacting Vitamin E with sodium phosphate. The '867 patent discloses how VEP can improve the health of animals when administered internally. Similarly, WO 93/15731 discloses how internally administering phosphate derivitized Vitamin E to mice can prevent liver damage. Unlike prior oil-soluble Vitamin E preparations, VEP is soluble in water.

Another conventional method to improve the appearance of the skin is to increase the natural exfoliation rate (cell renewal rate) of the outermost part of the stratum corneum, thus exposing lower layers of the stratum corneum, through the application of exfoliating acids. Unlike the previously discussed method of protecting living skin cells with oil-soluble Vitamin E and its oil-soluble. derivatives, here the exfoliating acids speed the; natural exfoliation process by acting on the layers of dead skin cells. Many exfoliating acids are known to increase the rate of natural exfoliation. Exfoliating acids include glycolic acid, lactic acid, citric acid, malic acid, tartaric acid, salicylic acid, acetic acid, pyruvic acid, poly hydroxy acids (including gluconolactone and derivatives) and the alpha and beta hydroxycarboxylic acids that have recently received an increasing amount of attention. The lower molecular weight, short chain acids, such as lactic and glycolic acid, are the exfoliating acids most widely used in cosmetics.

A significant drawback to the use of acids as exfoliating agents, including hydroxycarboxylic acids, is that they are most effective at low pH, about 4.0 or less. As disclosed in Yu, R. J., et al. "Bioavailability of Alpha-Hydroxy Acids in Topical Formulations," Cosmetic Dermatology, Vol. 9, No. 6 (June 1996), acidic exfoliating agents are believed to deprotonate at a pH of about 3.8, thus losing their beneficial activity at higher pH due to a lack of bioavailability. The inability of exfoliating acids to maintain their effectiveness at higher pH ranges was also demonstrated in Smith, W. P., "Hydroxy Acids and Skin Aging," Soap/Cosmetics/Chemical Specialties, pp. 54–58, 76 (September 1993).

Another drawback to the use of exfoliating acids is that a strong correlation exists between their ability to exfoliate (increase cell renewal rate) and the degree of skin irritation that results. This increased irritation is likely attributable to the acidity of the active agent. Therefore, for compositions relying on exfoliating acids to increase cell renewal rates, the degree of exfoliation increases with an increase in acidity and irritation. Thus, in actual use, the amount of beneficial skin exfoliation that an exfoliating acid can deliver may not be limited by the exfoliation ability of the acid, but by how often the composition can be applied to the skin without undue irritation.

As previously stated, at a pH of about 4.0 or less, exfoliating acids, which include hydroxycarboxylic acids, demonstrate a significant stimulation of cell renewal coupled with an undesirable level of skin irritation. However, as the pH of the acidic composition is increased to approach neutral (7.0), cell renewal, in addition to skin irritation, rapidly decreases. Thus, it would be beneficial to provide an exfoliating composition that increases the rate of natural skin exfoliation without the skin irritation associated with exfoliating acids. It would be most desirable to provide for enhanced skin exfoliation at a pH more closely approaching neutral to reduce skin irritation. Thee present compositions provide enhanced skin exfoliation at a higher pH and with lower irritation than conventional exfoliating acids, thus overcoming a significant disadvantage of acidic exfoliants.

SUMMARY OF THE INVENTION

In one aspect, the present invention provides a cosmetic or dermopharmaceutical composition for topical use comprising a water-soluble Vitamin E derivative and a carrier that includes water. The water-soluble Vitamin E derivative is preferably a water-soluble salt of Vitamin E and is in the water phase.

In another aspect, a water-soluble Vitamin E derivative is present in the composition in an amount effective to increase the rate of natural skin exfoliation at a pH that significantly reduces skin irritation in comparison with prior exfoliating acids. The water-soluble Vitamin E derivative enhances the rate of skin exfoliation without undue irritation.

In accordance with this aspect of the present invention, there is provided a composition including a water-soluble Vitamin E derivative present in a therapeutically effective amount in a, topically acceptable carrier for application to human skin to increase the natural rate of skin exfoliation. Preferably, the composition contains from about 0.05% to about 30% of a water-soluble Vitamin E derivative and has a pH in the range from about 4.5 to 9.

Another aspect of the present invention includes a method of increasing the rate of skin exfoliation comprising topically applying a cosmetic composition containing an amount of a water-soluble Vitamin E derivative effective to enhance the rate of skin cell exfoliation beyond the naturally occurring rate of skin cell exfoliation. In this aspect, the method includes topically applying to the skin a composition comprising a water-soluble Vitamin E derivative in an amount and for a period of time sufficient to increase the rate of natural skin exfoliation.

DETAILED DESCRIPTION OF THE INVENTION

The present invention relates to compositions that enhance the rate of skin cell renewal or exfoliation and to a method of increasing the skin cell renewal rate. The compositions are believed to act by increasing the exfoliation or "release" of dead cells, not by repairing or protecting living skin cells from damage, including oxidative damage from radicals and peroxides. Thus, the present compositions increase the rate at which dead keratinizing cells are released; they are not believed to protect living cells from damage.

In particular, the present invention relates to a composition containing a skin benefiting agent that includes a water-soluble Vitamin E derivative that stimulates cell renewal, but does not unduly irritate at the desired pH. In an especially preferred aspect, the present invention includes a composition including sodium phosphate derivatized Vitamin E (VEP). The present invention also relates to a method of increasing the rate of skin-cell exfoliation by applying a composition to the skin, wherein the composition comprises an effective amount of a water-soluble Vitamin E derivative and a carrier.

In accordance with one aspect of the present invention, a composition acceptable for topical application to the skin comprises a water-soluble Vitamin E salt and a carrier.

The water-soluble Vitamin E salts useful in the present invention include all enantiomers whether singly or in combination. With respect to the salts, preferable salts include phosphates and sulfates, with phosphate salts being presently preferred. The cation portion of the salt includes, but is not limited to alkali and alkaline earth metals such as sodium, potassium, calcium, and magnesium. The cations can be used alone or in a mixture of two or more. Sodium is a preferred cation for the salt.

Suitable water-soluble Vitamin E derivatives include, but are not limited to, Sodium Vitamin E Phosphate (VEP), Lauryl Imino Dipropionic Acid Tocopheryl Phosphate, Tocopheryl Glucoside, Tocopheryl Succinate, Tocophersolan (Tocopheryl Polyethylene Glycol 1000 Succinate), Tocophereth-5, 10, 12, 18, and 50 (polyethylene glycol (PEG) tocopheryl ethers). For the PEG vitamin E derivatives, increasing numbers represent increasing numbers of PEG molecules attached to the Vitamin E. Thus, as the number increases, so does water solubility, with Tocophereth-5 having the lowest water solubility and Tocophereth-50 having the greatest solubility in water. Preferred water-soluble Vitamin E derivatives include Sodium Vitamin E Phosphate (VEP) and Lauryl Imino Dipropionic Acid Tocopheryl Phosphate.

To prepare the compositions according to the present invention, at least one of the aforementioned water-soluble Vitamin E salts is mixed with a pharmaceutically or cosmetically acceptable carrier that includes water. Desirably, from about 0.05% to about 30% of the composition is the water-soluble Vitamin E derivative, more preferably from about 0.1% to about 15%. At present, a composition including from about 0.4% to about 5% of the water-soluble Vitamin E derivative is especially preferred. Unless stated otherwise, all percentages are given on a weight/weight basis.

Desirably, the carrier is capable of assisting in maintaining the desired pH of the composition. The pH values for the compositions of the present invention are from about 4.5 to about 9, preferably from 4.8 to 8.2, and more preferably from 5.6 to 7.9.

While the difference in the numerical value of these pH ranges is small, the difference in acidity is substantial because of the logarithmic relationship between numerical pH values and acidity. Thus, a pH of 5 is an order of magnitude less acidic than a pH of 4.

Desirably, the water-soluble Vitamin E derivative is not combined to form a composition containing exfoliating acids, squalene, or squalane. A "squalane" is a saturated hydrocarbon formed by reduction of squalene, an unsaturated hydrocarbon occurring. in fish and plant oils. In another aspect, the composition does not include an exfoliating acid at a concentration sufficient to provide an increase in exfoliation rate. In another aspect, the composition does not contain greater than 2% of an exfoliating acid. In yet another aspect, the composition does not contain an exfoliating acid having a bioavailability of 4% or greater, more preferably 1% or greater.

The compositions of the present invention may be formulated as a water-based solution, gel, lotion, cream, ointment, oil-in-water emulsion, water-in-oil emulsion, or other pharmaceutically acceptable form. If, however, the water-based composition contains oil, the water-soluble Vitamin E salt is substantially in the water phase.

The cosmetically acceptable carrier includes water and preferably acts as a dilutant, dispersant, or carrier for other cosmetic ingredients present in the composition, so as to facilitate their distribution when the composition is applied to the skin. Preferably, the composition includes from 5 to 98% water and more preferably from 80 to 98% water.

The compositions of the present invention may also contain various conventional cosmetic ingredients, so long as they do not detrimentally affect the desired enhancement of skin exfoliation or composition pH. Suitable cosmetic ingredients can include liquid or solid emollients, organic or inorganic sunscreens, preservatives, buffers, solvents, humectants, viscosity modifiers, alcohols, fats, oils, surfactants, fatty acids, silicone oils, moisturizers, emulsifiers, stabilizers, coloring agents and perfumes. The claimed compositions may also include propellants such as propane, isobutane, dimethyl ether, carbon dioxide, and nitrous oxide.

As used herein, "emollients" refer to materials used for the prevention or relief of dryness, as well as for the protection of the skin. Wide varieties of suitable emollients as described in Sagarin, Cosmetics, Science and Technology, 2nd Edition, Vol. 1, pp. 32–43 (1972), and incorporated herein by reference, are known and may be used herein.

The compositions can optionally include inorganic and organic sunscreens as cosmetic ingredients that provide protection from the harmful effects of excessive exposure to sunlight during use. In one aspect, preferable compositions include from 0.1 to 10% and more preferably from 1 to 5% of an organic sunscreen.

Examples of suitable organic sunscreens include those set out in Table 1 below, and mixtures thereof.

TABLE 1

| CTFA Name | Trade Name | Supplier |
|---|---|---|
| Benzophenone-3 | UVINUL ® M-40 | BASF Chemical Co. |
| Benzophenone-4 | SPECRA-SORB ® UV-24 | American Cyanamide |
| DEA Methoxycinnamate | BERNEL HYDRO ® | Bernel Chemical |
| Ethyl dihydroxypropyl-PABA | AMERSCREEN ® P | Amerchol Corp. |
| Glyceryl PABA | NIPA ® G.M.P.A. | Nipa Labs. |
| Homosalate | KEMESTER ® HMS | Hunko Chemical |
| Methyl anthranilate | SUNAROME ® UVA | Felton Worldwide |
| Octocrylene | UVINUL ® N-539 | BASF Chemical Co. |
| Octyl dimethyl PABA | AMERSCOL ® | Amerchol Corp. |
| Octyl methoxycinnamate | PARSOL ® MCX | Bernel Chemical |
| Octyl salicylate | SUNAROME ® WMO | Felton Worldwide |
| PABA | PABA ® | National Starch |
| 2-Phenylbenzimidazole-5-sulphonic acid | EUSOLEX ® 232 | EM Industries |
| TEA salicylate | SUNAROME ® | Felton Worldwide |
| 3-(4-methylbenzylidene)-camphor | EUSOLEX ® 6300 | EM Industries |
| Benzophenone-1 | UVINUL ® 400 | BASF Chemical Co. |
| Benzophenone-2 | UVINUL ® D-50 | BASF Chemical Co. |
| Benzophenone-6 | UVINUL ® D-49 | BASF Chemical Co. |
| Benzophenone-12 | UVINUL ® 408 | BASF Chemical Co. |
| 4-Isopropyl dibenzoyl methane | EUSOLEX ® 8020 | EM Industries |
| Etocrylene | UVINUL ® | BASF Chemical Co. |

The claimed compositions may also contain an inorganic sunscreen, which includes, but is not limited to titanium dioxide; zinc oxide, having an average particle size of from 1 to 300 nm; iron oxide, having an average particle size of from 1 to 300 nm; and silica, such as fumed silica, having an average particle size of from 1 to 100 nm. The total amount of titanium dioxide that can be incorporated in the composition is from 1 to 25%, preferably from 2 to 10%, and ideally from 3 to 7%.

It may also be desirable to incorporate anti-inflammatory and/or anti-irritant agents into the claimed compositions. The natural anti-inflammatory and/or anti-irritant agents are preferred. For example, licorice and its extracts, dipotassium glycyrrhizinate, oat and oat extracts, candelilla wax, alpha bisabolol, aloe vera, Manjistha (extracted from plants in the genus Rubia, particularly Rubia cordifolial), and Guggal (extracted from plants in the genus Commiphora, particularly Commiphora Mukul), may be used.

Additional skin benefit agents such as ceramides, glycoceramides, pseudoceramides, sphingolipids such as sphingomyelins, cerebrosides, sulphatides, and ganglioside, sphingosines, dihydrosphingosine, phytosphingosines, and phospholipids, may also be incorporated into the claimed compositions, either separately or in mixtures. Fatty acids may also be combined with these skin benefit agents. For example, the ceramides and glycoceramides include those described in U.S. Pat. Nos. 5,589,178, 5,661,118, and 5,688,752, the relevant portions of which are incorporated herein by reference. For example, the pseudoceramides include those described in U.S. Pat. Nos. 5,198,210; 5,206,020; and 5,415,855, the relevant disclosures of which are incorporated herein by reference.

In accordance with one aspect of the present invention, the rate of natural skin exfoliation may be increased by topical application to the skin of the claimed compositions. In this regard, the present invention encompasses a method of enhancing the rate of natural skin exfoliation including topically applying to the skin a composition comprising a water-soluble Vitamin E derivative (salt) in an amount and for a period of time sufficient to increase the rate of natural skin exfoliation. In another embodiment, the Vitamin E salt is provided in a carrier that includes water and that is capable of assisting in maintaining the desired composition pH.

Generally, the topical composition is applied on at least a daily basis and may be applied for any suitable period of time. In comparison to conventional acidic (pH<4.0) compositions, the compositions of the present invention may be applied on a more regular basis with substantially reduced irritation to the skin. While not wishing to be bound by any particular theory, the reduction in skin irritation achieved during enhanced exfoliation, which the claimed compositions can provide, is believed attributable to the compositions having a pH more closely approaching that of human skin (pH~5) and higher. By applying the present compositions on a routine basis to the skin, within a few days, a user may notice improved skin texture and smoothness with reduced irritation.

Table 3 sets forth a comparative study between the cell-renewal rates of a water-soluble Vitamin E derivative (VEP, a sodium-phosphate salt) and a conventional exfoliating acids (Lactic Acid). Skin irritation, expressed as a "Sting" percentage, was also determined. The increase in skin cell renewal rate and irritation level was measured substantially according to the procedure described in Soap/Cosmetics/Chemical Specialties for September 1993 at pp. 54–58 and 76.

TABLE 3

| Active Ingredient | Amount (wt %) | Composition pH | Cell-Renewal Rate % | Irritation Level (Sting %) |
|---|---|---|---|---|
| Lactic Acid | 5 | 3 | 31.7 | 194.7 |
| VEP | 0.5 | 5.65 | 15.2 | 17.3 |
| VEP | 1.0 | 7.21 | 16.6 | 10.7 |
| VEP | 2.0 | 7.78 | 22.8 | 24.0 |
| VEP | 2.0 | 7.78 | 21.4 | 37.3 |

As can be seen from the table, when VEP is compared to the lactic acid control, beneficial cell-renewal rates are achieved at surprisingly low sting percentages. The results clearly establish that skin exfoliation (cell-renewal rate %) increases with higher concentrations of VEP and with increasing pH. Thus, the ability of the water-soluble Vitamin E to exfoliate at pH levels above 4.0, where conventional acidic exfoliating agents loose their activity, is established. While the previously mentioned exfoliating acids, such as lactic acid, salicylic acid, and the alpha and beta hydroxy-carboxylic acids, are commonly thought of as effective exfoliating agents, the discovery that a water-soluble Vitamin E derivative could serve as an effective exfoliating agent at high pH, above 4.5, was quite surprising.

It is clear from this data that the compositions of the present invention can provide beneficial exfoliation rates above pH 4.5. In fact, desirable cell renewal rates are seen at pH of about 5.6 and higher, and at pH values of about 7.2 and higher. This is quite surprising because conventional exfoliating agents not only lose their effectiveness above pH 4.0, but provide increased exfoliation rates with decreasing pH. In contrast to conventional exfoliants, the compositions of the present invention provide beneficial exfoliation above pH 4.5 and continue to increase their exfoliation performance with rising pH—a result completely opposite and unexpected to the results achieved with conventional acidic compositions.

While Sting results are somewhat subjective, as evidenced by the variance between the 2.0 (wt %) VEP results from Table 3, the results clearly show that while VEP is somewhat slower than Lactic Acid at cell-renewal, it is at least 4.5 times less irritating to the skin. In fact, at pH 7.21 for example, the present composition is about one-twentieth as irritating to the skin. Preferably, the claimed compositions can reduce consumer perceived skin irritation (Sting %) by at least 25% and more preferably by at least 50% in relation to results achieved with an exfoliating acid having a pKa of 4.0 and below.

Due to the significantly decreased skin irritation provided by water-soluble Vitamin E derivatives in relation to exfoliating acids, the present compositions can be used more often and more regularly than conventional acid-based exfoliating compositions to improve the skin. Thus, in actual use the present compositions can provide an overall increase in the rate of skin cell-renewal when compared with compositions containing exfoliating acids because the claimed compositions can be applied more frequently with reduced irritation.

The following are illustrative examples of formulations according to the invention. Although the examples use only selected compounds and formulations, it should be understood that the following examples are illustrative and not limited. Table 4 presents several examples of proposed solution and/or gel formulas falling within the scope of the present invention with the amounts provided being expressed as weight percent.

TABLE 4

| Ingredients | A | B | C | D |
|---|---|---|---|---|
| Water | 80.25 | 75.00 | 79.00 | 81.65 |
| VEP | 0.5 | 1.0 | 2.0 | 2.0 |
| Butylene Glycol | 2.0 | 1.0 | 3.0 | 3.0 |
| PEG-8 | | 2.0 | | |
| Glycerin | 1.0 | 2.0 | 2.0 | 4.0 |
| Glycereth-26 | 1.0 | 2.0 | 2.0 | |
| Sodium Hyaluronate (0.5% soln) | 0.2 | 0.4 | | 0.2 |
| Dipotassium Glycyrrhizinate | 0.01 | | | |
| Panthenol | 0.25 | 0.25 | | 0.5 |
| Oat Extract | 2.0 | | 1.0 | |
| Cucumber Extract | 2.0 | | 1.0 | |
| Alcohol | 2.0 | 8.0 | 4.0 | |
| Thickeners, extracts, preservatives, emulsifiers, skin conditioners, neutralizers | 8.79 | 8.35 | 6.0 | 8.65 |
| Total | 100.00 | 100.00 | 100.00 | 100.00 |

Table 5 presents several examples of proposed emulsion, cream, and/or lotion formulas falling within the scope of the present invention with the amounts provided being expressed as weight percent.

TABLE 5

| Ingredients | A | B | C | D |
|---|---|---|---|---|
| Water | 59.6 | 58.36 | 70.42 | 67.25 |
| VEP | 0.5 | 1.0 | 2.0 | 2.0 |
| Silicone Elastomers | 25.0 | | 4.0 | |
| Butylene Glycol | | 4.0 | 1.5 | 5.0 |
| Glycerin | 1.0 | 0.5 | 1.0 | 0.5 |
| Glycereth-26 | 1.0 | | 2.0 | |
| Sodium Hyaluronate (0.5% soln) | | 0.50 | 0.50 | 0.50 |
| Dipotassium Glycyrrhizinate | | 0.02 | 0.01 | |
| Panthenol | | 0.1 | 0.05 | 0.1 |
| C12–15 Alkyl Benzoate | | | 5.0 | 2.0 |
| Tocopherol | | 0.1 | 0.05 | 0.1 |
| Caprylic/Capric Triglyceride | | 5.0 | | |
| Octyl Methoxycinnamate | | 2.0 | | |
| GMS & PEG-100 Stearate | | 5.0 | 4.25 | 5.0 |
| Cetyl Alcohol | | 1.0 | | 2.5 |
| Titanium Dioxide | | 3.5 | | |
| Tetrasodium EDTA | | 0.2 | 0.1 | 0.2 |
| Oat Extract | 5.0 | 0.5 | 1.0 | |
| Phospholipids, Sphingolipids, Cholesterol | 1.0 | 0.5 | 0.35 | 0.1 |
| Thickeners, extracts, preservatives, emulsifiers, skin conditioners, neutralizers | 6.9 | 17.72 | 7.77 | 14.75 |
| Total | 100.00 | 100.00 | 100.00 | 100.00 |

It should be understood that a wide range of changes and modifications can be made to the compositions and methods of this invention. It is therefore intended that the foregoing description illustrates rather than limits this invention, and that it is the following claims, including all equivalents, which define this invention.

What is claimed:

1. A method of enhancing the natural rate of mammalian skin exfoliation comprising topically applying to the skin a composition comprising from 0.05% to about 30% of a water-soluble Vitamin E derivative wherein the water soluble Vitamin E derivative is selected from the group consisting of Sodium Vitamin E Phosphate, Lauryl Imino Dipropionic acid Tocopheryl Phosphate, Tocopheryl Glucoside, Tocopheryl Succinate, Tocophersolan (Tocopheryl Polyethylene Glycol 1000 Succinate), Tocophereth-5, Tocophereth-10, Tocophereth-12, Tocophereth-18, Tocophereth-50, and mixtures thereof and a carrier comprising water, wherein the composition has a pH from about 4.5 to 9.

2. The method of claim 1, wherein the water-soluble Vitamin E derivative is selected from the group consisting of Sodium Vitamin E Phosphate, Lauryl Imino Dipropionic Acid Tocopheryl Phosphate, and mixtures thereof.

3. The method of claim 1, wherein the water-soluble Vitamin E derivative is Sodium Vitamin E Phosphate.

4. The method of claim 1, wherein the composition comprises from 0.1% to about 10% of the water-soluble Vitamin E derivative.

5. The method of claim 1, wherein the composition further comprises a cosmetic ingredient.

6. The method of claim 1, wherein the composition has a pH from 4.8 to 8.2.

7. The method of claim 1, wherein the composition has a pH from 5.6 to 7.9.

8. The method of claim 1, wherein the natural rate of skin exfoliation is accelerated by at least 10%.

9. The method of claim 1, wherein the natural rate of skin exfoliation is accelerated by at least 15%.

10. The method of claim 1, wherein the natural rate of skin exfoliation is accelerated by at least 20%.

11. The method of claim 1, wherein sting % is reduced by at least 25% in relation to that achieved with an exfoliating acid having a pKa of 4.0 and below.

12. The method of claim 1, wherein sting % is reduced by at least 50% in relation to that achieved with an exfoliating acid having a pKa of 4.0 and below.

13. The method of claim 1, wherein the natural rate of skin exfoliation is accelerated by at least 10% and sting % is reduced by at least 25% in relation to that achieved with an exfoliating acid having a pKa of 4.0 and below.

14. The method of claim 1, wherein the natural rate of skin exfoliation is accelerated by at least 20% and sting % is reduced by at least 50% in relation to that achieved with an exfoliating acid having a pKa of 4.0 and below.

15. The method of claim 1 wherein the composition is formulated as a solution, gel, lotion, cream, or ointment.

16. The method of claim 1 wherein the topical application: is on at least a daily basis.

* * * * *